United States Patent [19]

Anderson et al.

[11] Patent Number: 5,301,560

[45] Date of Patent: Apr. 12, 1994

[54] CLOSED LOOP LIQUID SAMPLER AND SAMPLING SYSTEM

[75] Inventors: John D. Anderson, Lake Jackson; Charles R. Boyd, Victoria, both of Tex.

[73] Assignee: Texas Sampling, Inc., Houston, Tex.

[21] Appl. No.: 795,969

[22] Filed: Nov. 22, 1991

[51] Int. Cl.⁵ ............................................. G01N 1/00
[52] U.S. Cl. ................................................ 73/863.86
[58] Field of Search ........... 73/863.86, 864.14, 864.15, 73/863.72, 863.81, 864.61, 863.01; 137/68.1, 876, 887; 604/411, 414, 415; 141/2, 18, 21, 329, 330, 383, 386

[56] References Cited

U.S. PATENT DOCUMENTS

| | | | |
|---|---|---|---|
| 1,534,939 | 4/1925 | Fuge . | |
| 1,842,134 | 1/1932 | Waite . | |
| 2,475,857 | 7/1949 | Reinert . | |
| 2,693,705 | 11/1954 | Casler et al. | 73/864.51 |
| 2,797,150 | 6/1957 | Rigby . | |
| 2,844,964 | 7/1958 | Guibert | 73/863.86 |
| 3,276,265 | 10/1966 | Taft . | |
| 3,383,923 | 5/1968 | Conche et al. . | |
| 3,438,263 | 4/1969 | Webb . | |
| 3,484,849 | 12/1969 | Huebner et al. | 604/201 |
| 3,719,086 | 3/1973 | Bannister et al. . | |
| 3,776,042 | 12/1973 | Werra et al. | 73/863.85 |
| 3,872,730 | 5/1975 | Ringrose et al. | 73/864.23 |
| 3,882,909 | 5/1975 | Ogle | 141/286 |
| 4,014,216 | 5/1977 | Thornton et al. | 73/864.21 |
| 4,118,987 | 10/1978 | Zeh | 73/863.61 |
| 4,174,632 | 12/1979 | Jansen | 73/863.86 |
| 4,252,021 | 2/1981 | Drushel | 73/863.86 |
| 4,296,786 | 10/1981 | Brignola | 141/309 |
| 4,380,176 | 4/1983 | Bauer et al. | 73/863.86 |
| 4,461,185 | 7/1984 | Schoffel | 73/864.01 |
| 4,505,709 | 3/1985 | Froning et al. | 604/411 |
| 4,532,969 | 8/1985 | Kwaan | 141/27 |
| 4,580,542 | 4/1986 | Masson | 73/863.86 |
| 4,651,574 | 3/1987 | Spencer | 73/863.86 |
| 4,749,658 | 6/1988 | Jaekel et al. | 73/863.72 |
| 4,791,821 | 12/1988 | Spencer | 73/863.86 |
| 4,879,915 | 11/1989 | Spencer | 73/864.74 |
| 4,887,472 | 12/1989 | Jansen | 73/863.86 |
| 4,986,138 | 1/1991 | Spencer | 73/863.86 |
| 5,088,996 | 2/1992 | Kopfer et al. | 604/411 |
| 5,122,129 | 6/1992 | Olson et al. | 604/411 |

FOREIGN PATENT DOCUMENTS

| | | |
|---|---|---|
| 2907558 | 2/1979 | Fed. Rep. of Germany . |
| 549706 | 6/1977 | U.S.S.R. . |
| 823950 | 4/1981 | U.S.S.R. . |
| 8900284 | 1/1989 | World Int. Prop. O. ....... 73/863.01 |

Primary Examiner—Hezron E. Williams
Assistant Examiner—Nashmiya Ashraf
Attorney, Agent, or Firm—Pravel, Hewitt, Kimball & Krieger

[57] ABSTRACT

The invention relates to a sampler mechanism for fluidly interconnecting a ball valve with the interior space of a septum closed container for the taking of closed loop samples of fluid materials. The sampler mechanism includes a needle assembly having a hollow needle and a needle seating collar which is positioned adjacent the ball in the ball valve, a threaded injector end fitting for attaching and securing the needle assembly to the ball valve, and an injector body for fluidly connecting the ball valve to the container and for providing a fluid passageway for fluid communication between the container and a side surface of the injector body.

8 Claims, 6 Drawing Sheets

FIG. 7

CLOSED LOOP LIQUID SAMPLER AND SAMPLING SYSTEM

FIELD OF THE INVENTION

This invention relates to a mechanism by which a liquid sample can be drawn into a septum closed sample container without exposing such sample to the atmosphere or the operator taking such sample.

BACKGROUND OF THE INVENTION

In the operation of many chemical and other processes it is often necessary to periodically sample fluids which are flowing within the process at various points. Many process fluids present serious safety hazards when released or exposed to the atmosphere. Other process fluids, although not extremely hazardous or toxic, may be highly water sensitive for absorption of atmosphere moisture which makes it impossible to obtain an accurate moisture analysis if the sample is exposed to the atmosphere. For a multitude of reasons, it is desired to obtain various process fluid samples in a closed loop manner which does not permit exposure of the sample fluid to the atmosphere.

Heretofore, a variety of devices and mechanisms have been disclosed for the purpose of obtaining closed loop samples. U.S. Pat. No. 2,693,705 discloses a liquid sampler for the sampling of radioactive, poisonous or valuable liquids for analytical purposes. This patent discloses a sampler device by which, through the operation of an air pressure aspirator, a sample is drawn by aspiration from a sample point through an injection needle into a septum closed sample container and liquid overflow beyond a preset sample amount are aspirated from the sample container back into the line from which the sample is taken. A closed loop sampler of this design requires a source of pressurized air for its proper operation and is generally designed for small sample volumes.

Other closed loop sampling devices which have heretofore been described utilize the pressure of the sample in the sample line as the driving force by which a liquid sample is propelled into the sample container. In the design disclosed by U.S. Pat. No. 4,174,632, there is disclosed a closed loop sampling device comprising a valve having integrally formed with the body thereof a cap which receives a sample container the external surface of which corresponds to the internal configuration of the cap, an injection needle is disposed within the cap and is in fluid communication with the valve. A sample is taken by moving a sample container having a septum closure through the open end of the cap, the cap properly positions the container for penetration of the septum, and pressing it upwards against the injection needle to penetrate the septum. When so configured the valve is turned on into communication with the needle and the sample passes from the line through the needle into the sample container. For purposes of venting the sample container as it fills with liquid, a second or vent needle may be provided within the cap which communicates vented vapor back to the process or to a special storage area. In such a device as disclosed, because the cap is integrally formed with the valve body, should a sample needle or a vent needle become clogged and need cleaning or replacement, the entire sampling device comprising the valve with integrally formed cap and needles thereof requires replacement. Further, because the cap is integrally formed with the valve body, the sampler is specific to a single size of sample container.

U.S. Pat. No. 4,887,472 discloses a closed loop sampler which in part comprises a hood having a sampling and venting needle integrally formed therewith, one end of said hood is thread mounted to a valve, the other end of said hood is mounted with a reciprocating sleeve which receives a septum closed sample container, the lower end of the said hood is itself sealed with a septum. A sample is taken by reciprocating the sleeve with sample container upward towards the valve causing the two needles to penetrate the first septum which seals the hood itself, and further the septum of the sample container. The valve is then operated, a sample taken and upon completion of the sample, the sleeve is reciprocated downward whereby the needles are withdrawn from penetration of the septum of the sample container as well as the lower septum of the hood. A fluid may then be circulated into the sealed area around the needles defined by the lower septum of the hood and the needles washed of old sample before a new sample is taken. Again, because of the integral formation of the sample and vent needles with the hood, should one or both needles become clogged, it is necessary to replace the entire hood mechanism of this sampler.

In yet other closed loop sampler mechanisms as disclosed in U.S. Patent Nos. 4,651,574; 4,791,821 and 4,879,915, a sampling device is disclosed, the key element of which is a unitary needle body having in a single needle stem a sample fluid passageway and a vent gas passageway. The sample fluid passageway communicates the needle tip to the valve whereas the vent passageway communicates the needle tip to a side location of the needle body which is internally threaded to receive a fitting connection. The upper portion of this needle body is threaded directly to a valve and to the lower portion of the needle body a sample container hood is threaded. A fluid sample is taken by passing a septum closed sample container through the lower end of the hood, pressing its septum against the needle stem and opening the valve until a desired amount of sample fluid is obtained.

Each of the types of closed loop samplers heretofore disclosed entail various disadvantages. The aspirated dual needle constant volume design of U.S. Pat. No. 2,693,705 requires the presence of an aspirator unit and a source of external compressed air, which both complicates and renders more expensive the design of such unit and its operation. In the sample devices of U.S. Pat. No. 4,174,632 and 4,887,472, the sample and vent needles are not separately serviceable for repair/cleaning or replacement. Further, when installing such a sampler, the proper positioning of the vent gas port is obtained in the case of the '632 design by reason of its manufacture as an integral part of the valve. In the design of the '472 patent, since the hood element carries the ventway passage port and the hood element is itself directly threaded to the valve, proper positioning of the vent gas port is a matter of proper thread design of the threaded portion of the hood body. That is, the valve fitting threads must be designed to secure a fluid tight fastening of the hood to the valve body at a point wherein when proper fastening is obtained, the vent passageway port is properly positioned. Accordingly, this renders the manufacture and on site installation of such device to be more difficult. In the dual passageway, single needle body design of U.S. Pat. Nos. 4,651,574; 4,791,821 and 4,879,915, the needle stem must be of a sufficiently large diameter to accommodate the two passageways therethrough. This, unfortunately, renders penetration of the septum of the sample container to be more difficult and further introduces a larger than desirable perforation to the septum which may not properly reseal upon removal of the sample container from the needle stem.

Further, by and large, such closed loop sampler devices as have heretofore been disclosed require custom installation by the process operator. That is, the user of the device is required to custom install the device with the necessary sample fluid conduit line and the vent gas conduit line. The installation of a plurality of even the same types of a device throughout a process unit often lacks any degree of uniformity.

It is desirable to develop a closed loop fluid sampling device which permits sampling of fluid flow within a process line without the need for a separate pump or aspirator as a part of the device; which permits ready removal, repair and replacement of the sample and/or vent needles of the device; permits of the sample/vent needles to be constructed of a different material from other non-wetted parts of the device; which allows for the taking of samples of differing volumes as desired; and which eliminates or reduces dead volume within the device wherein a portion of processes fluid taken from a previous sample may be held up within the device to contaminate a new portion of process fluid when a subsequent sample is taken. It is further desired to develop a self-contained sampling system unit which is adapted to easy and uniform installation by the simple expedient of positioning and line fitting connection of the unit at a sample point within a processing unit.

SUMMARY OF THE INVENTION

This invention comprises a mechanism and a system for the taking of closed loop sample of fluid materials.

The mechanism comprises a process needle assembly and an injector end fitting by which the mating end of a sample needle is brought into almost direct contact with the ball of a ball valve and secured to the valve body; an injector body with a receiving cavity at its first end which is communicated to its second end by a bore through which the sample needle passes; said injector body being freely rotatable about said injector end fitting until affixedly secured thereto by locking screws; said injector body having a plurality of passageways which communicate its second end to an exterior surface of said body which is at a point intermediate between the first and second end of said injector body, each terminus of said passageways preferentially being internally threaded. Preferably the mechanism further comprises a second or vent needle which carries a ferrule at its mating end and which is secured to the terminus of a passageway at the second end of said injector body by a vent needle locking nut which is externally threaded about its first end which has an internal ferrule receiving surface, said vent needle passing through an orifice which communicates the first end of said vent locking nut to the second end of such nut, the external surface of the second end being of a configuration adapted to receive a tool in mating engagement.

The injector body of this invention preferably has a first and second externally threaded surface, the first externally threaded surface being located at a point intermediate between the second end of said body and said receiving cavity end of said body and a second threaded exterior surface which is contiguous with the second end of the said body, said first externally threaded surface being of a diameter larger than said second externally threaded surface. Preferably said device further comprises a docking ring cap having an internally threaded surface contiguous with and extending from its first end towards its second end, and a second end which carries a radially inwardly projecting lip which defines an orifice through which said sample needle and vent needle can extend. Said docking ring cap is securely affixed to said second externally threaded surface of said injector body and when so affixed provides a flat stopping surface by which the septum closed cap of a sample container is stopped in a position wherein said first and second needles are in true perpendicular perforating contact with said septum of the sample container.

Said device preferably further comprises a shroud, one end of which has an internally threaded surface which corresponds to and is adapted for attachment to said first externally threaded surface of said injector body, and a second open end through which a septum closed sample container can be passed into contact with the sample/vent needles of said device.

The mechanism of the invention preferably further comprises means within the shroud for securing therein rings of varying internal diameters by which the sampling device can be adapted to receive sample containers of various external diameters. Preferentially, said shroud further carries a pivoted sample container support strap which can be moved in a position to support a sample container once inserted into said shroud and hold such container there until the sampling process is complete.

In one mode of operation, a sampling device as above described can be communicated with a purge fluid through one of the passageways extending through the injector body thereof and a purging fluid can, when necessary, be communicated over the sample container within the shroud in the event of an accidental spill of sample fluid upon the sample container. In an alternative embodiment, the lower end of the purge fluid passageway of the injector body can be supplied with a third needle whereby, when a sample container is properly positioned within the shroud the third needle penetrates the septum and gas, such as dry nitrogen, can be circulated continuously through the sample container to insure that it is purged of any moisture content or oxygen content after which, said purge gas can be blocked and a fluid sample taken without contacting said fluid sample with oxygen or moisture.

This invention further comprises the utilization of the inventive sampling device in assembly on a panel board with a filtering device, which is preassembled with fitting connectors and fluid conduits which appropriately communicate the process sample line with the valve inlet and outlet, and which communicate the sample device vent gas outlet to the filtering device. The system provides a self-contained ready to install sampling unit. The necessary conduits are carried on the back of the panel and the conduit which carries fluid from the process sample point to the sampler valve may be configured to provide for heat exchange of the process fluid before sampling, as needed, by a heat exchange medium. The back of the panel may be, and preferably is provided with mounting means, such as bolt fastened U brackets by which the panel may be readily mounted to a stanchion or other support structure. If desired, the panel may be mounted within a housing having front and back doors for protection of the devices thereof from the surrounding environment.

BRIEF DESCRIPTION OF THE DRAWINGS

In the FIGS. which illustrate the device and system of this invention like parts are similarly numbered.

DETAILED DESCRIPTION OF THE PREFERRED EMBODIMENTS

The closed loop liquid sampler of this invention allows an operator to obtain accurate and reliable samples from process streams, such as benzene, toluene, xylene and other hazardous, toxic or water sensitive compounds with maximum operator safety and minimum or zero emissions and exposure of the sample to the atmosphere. The new sampler mechanism eliminates problems experienced by prior sampling devices such as non-replaceable needles, sample dead volume contamination, sample bottle availability and versatility, the inability to continually purge a sample container with an inert gas, and lack of accurately guiding of a sample bottle to process and vent needles.

In its most basic embodiment, the device of this invention, apart from the valve with which it operates, comprises a process needle assembly and an injector end fitting by which the process needle assembly is secured to the body of a ball valve such that the mating end of the needle is brought into almost direct contact with the ball operator of said valve. By this means, dead space is substantially eliminated and a means is provided for the ready removal of the needle for repair, replacement or a change to a needle of a longer size, different diameter, or a different construction material.

Preferentially, the device further comprises an injector body having a first and second end, the first end being formed with a receiving cavity for receiving the lower end of the injector end fitting, a central axial orifice which communicates the receiving cavity to the second end of said injector body, the injector body having a first fluid passageway which communicates the second end of said body to a side surface of said body at a point intermediate between the first and second ends, a second fluid passageway which communicates the second end of said body to a side surface of said body at a point intermediate between the first and second ends, and at least one end of said first and second passageways is interiorly threaded at its terminus with the second end of said body. When assembled with injector end fitting body which carries the process needle assembly, the process needle passes through the central axial orifice and the injector body is freely rotatable about the injector end fitting until locked in place with a locking means, such as locking screws. This facilitates installation of a sample device by allowing the fluid passageways of the injector body to be located to any position desired for their later receipt of a line fitting. Further, the injector body is provided with a second needle carried by the terminus of one of the fluid passageways at the second end of said injector body and is removably affixed therein by a locking nut assembly which seats to a ferrule carried by the mating end of said second needle.

Preferentially, the device further comprises a docking collar which is secured to an externally threaded surface which is contiguous with the second end of said injector body and the ring at its lower end carries a radially inward projecting lip, the periphery of which defines an orifice through which the first and second needles of such device extend. The lip of the docking collar provides a stopping surface for the cap of a septum closed sample container which insures that said container stops in square contact with the docking collar such that the penetration of the needles through the septum is essentially perpendicular. This feature insures the smallest diameter of perforation in the septum by the needles, thereby increasing the reliability that the septum will properly reseal upon removal of the sample container.

Preferentially, the device further comprises a shroud body having a first end which contains an internally threaded surface adapted to be secured to an externally threaded surface of the injector body, the second end of said shroud body being open for purposes of passing a sample container through the shroud and into contact with the needles of the device. Most preferably the shroud body is provided with means to receive within its internal area, inserts of varying inside diameter by which means a shroud body can be accommodated to sample containers of various diameters while insuring proper targeting, docking and penetration by the needles of the device of the septum of the sample container.

When assembled with a valve, the components above described constitute an operative closed loop fluid sampling device.

Preferably, a closed loop fluid device of this invention is employed in a sampler system comprising, the closed loop fluid sampler device of this invention and a vent gas filter, each secured by appropriate means to a control panel, the front side of said panel carrying the closed loop fluid sampler device and the filter, the back side of the panel carrying the conduits which communicate the valve of the sampler device to a fitting for connection to a process sample point, and conduits which communicate the vent passageway of the injector body of said device to the filter. Further, the panel may be provided with a tube line which communicates a fitting to the second passageway of the injector body of the device, by which a purge fluid under valve control may be communicated to the internal area of the sample container shroud, or if the terminus end of this passageway is provisioned with a third needle for penetration of the septum of a sample container, to communicate a purge gas to and through the sample container as desired. Wherein the fluid to be sampled at a sample point is at a temperature in excess of that which can be tolerated by the septum of a sample container, the tube line by which the process sample point is communicated to the inlet of the valve of the device, may be of an extended length, and fashioned in a coiled or serpentine arrangement and supplied with a means of heat exchange—i.e., exposed to air or other cooling fluid—to cool the sample to a temperature appropriate for sample collection.

As other features of the closed loop fluid sampler device and the system are described in greater detail with reference to the drawings, further and additional advantages of this invention will become apparent.

Figure 1:
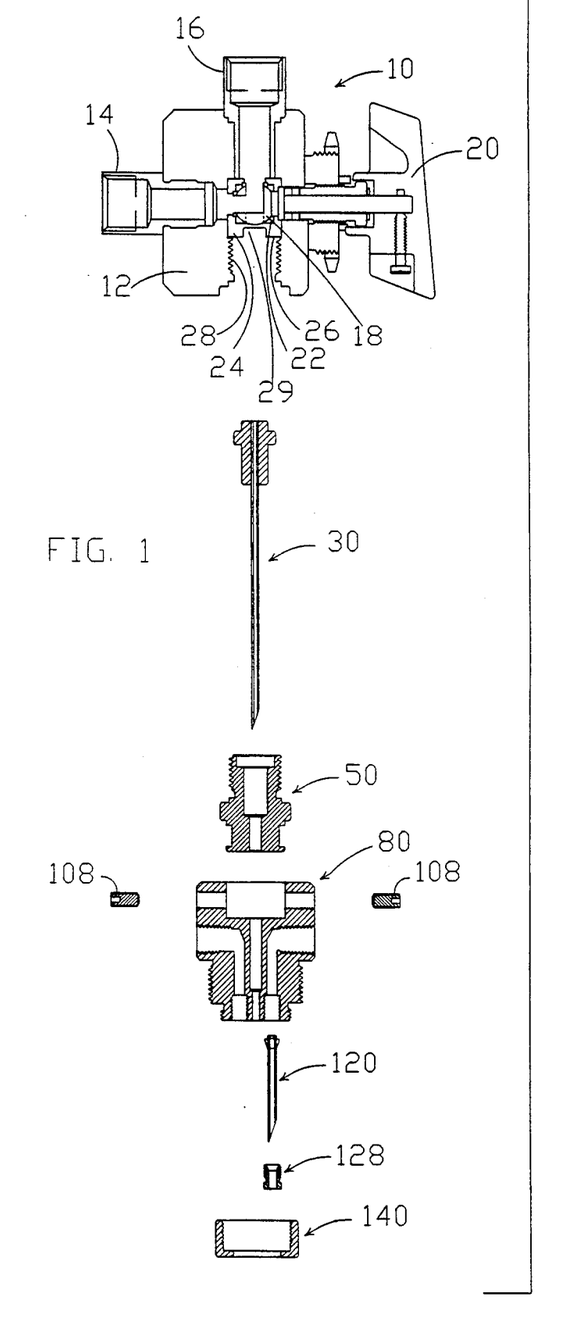
FIG. 1 is an exploded view in cross-section of a standard three-way ball valve as it would become associated to the component parts forming the mechanism of this invention, and particularly illustrates the operative position of the mating end of the sample needle assembly with respect to the ball operator of the ball valve which is effectuated by the assembly.

FIG. 1 illustrates in exploded view, the basic and preferred components of this invention with reference to their manner of assembly with a standard ball valve 10. The ball valve 10 is illustrated as fitted with a valve inlet fitting 14 and a valve outlet compression fitting 16 (such as a "Swagelok" fitting, for example) by which the valve may be communicated to the flow of a process line as a sample point valve. Ball valve 10 comprises a valve body 12 which has an internally threaded recess 28 for receipt of a valve fitting, a ball 18 and a handle operator 20 by which the positioning of ball 18 is controlled. The ball is secured within the valve body by a seat retainer 24 which carries a valve seat 22 upon which the ball rides which functions as a seal. The seat retainer is secured within the valve body by a washer 26. This washer defines a surface against which any end fitting which is threaded into recess 28 will stop. There is, accordingly, a chamber 29 defined between the end of such fitting and ball 18 which is a dead hold-up space for liquid from a previous sample once the ball is positioned for liquid flow from inlet 14 to outlet 16.

Further, with reference to FIG. 1, a process needle assembly 30 and an injector end fitting 50 are illustrated and both are further described with reference to FIG. 2. Fitted to the lower end of injector end fitting 50 and affixed thereto by locking screws 108 is injector body 80. Secured to the lower end of a passageway within injector body 80 is a second or vent needle 120 which is affixed thereto by a locking nut 128. Further, affixed about the exterior of the lower end of injector body 80 is docking collar 140. The injector body, second needle and its locking nut, and docking ring are described in further detail with reference to FIG. 3.

Figure 4:
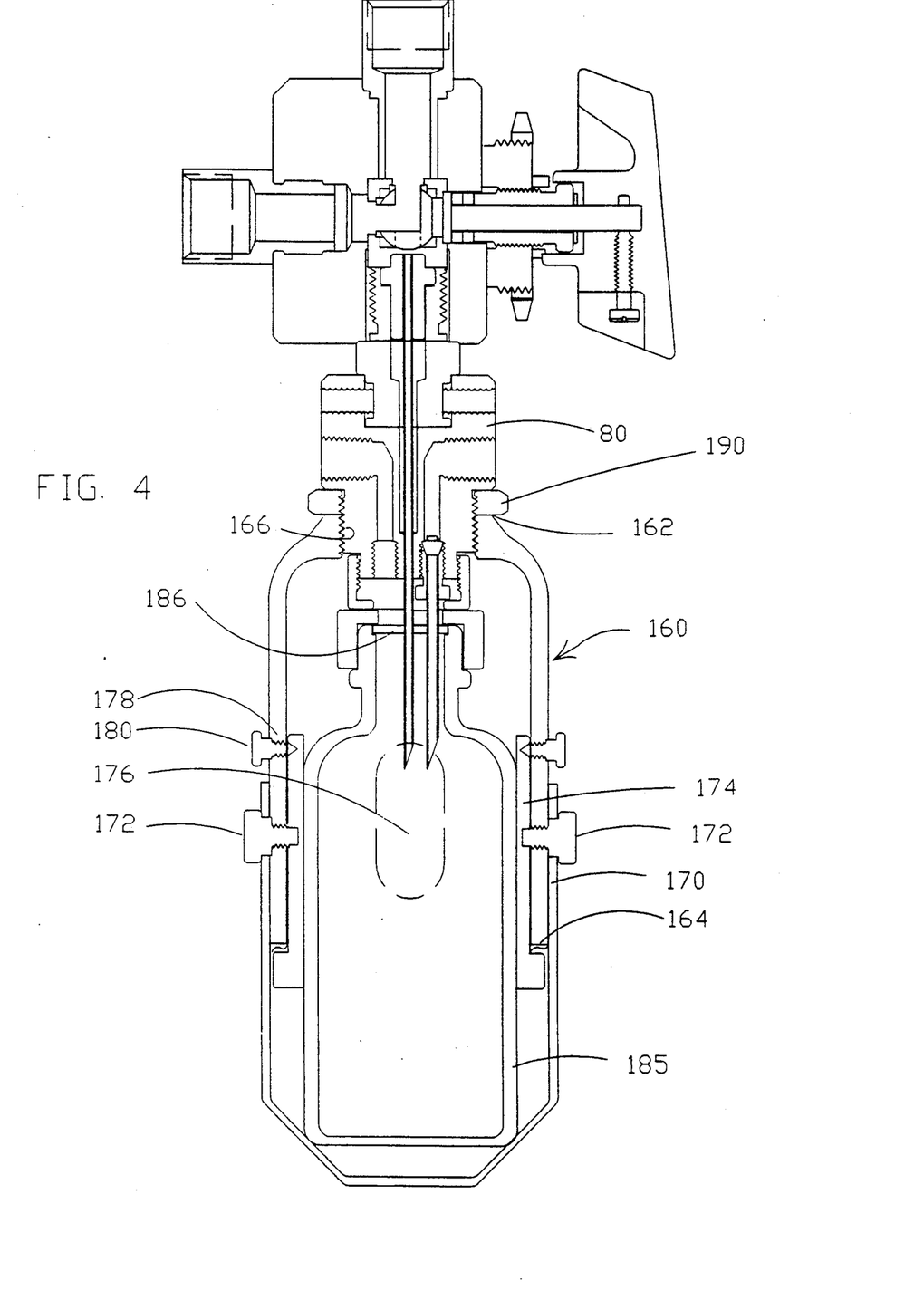
FIG. 4 illustrates in cross-sectional view, as operatively assembled with a ball valve, the process needle assembly, injector end fitting, injector body, vent needle assembly and docking ring as further assembly with a sample container shroud which is adapted to receive and retain ring inserts of various internal diameters to accommodate the use of sample containers of various diameters.
Figure 5:
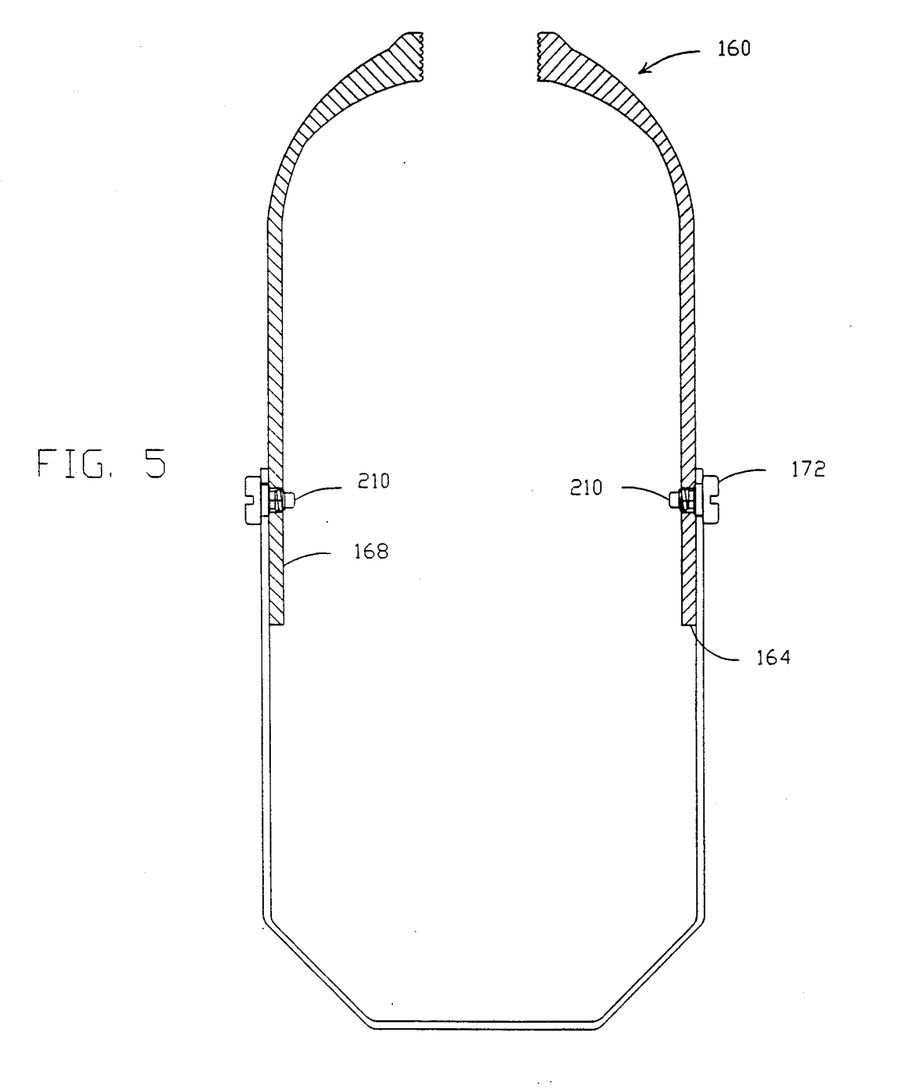
FIG. 5 illustrates in cross-sectional view an alternative embodiment of a sample container shroud which is designed to receive and retain a spring loaded and locking ring insert.
Figure 6:
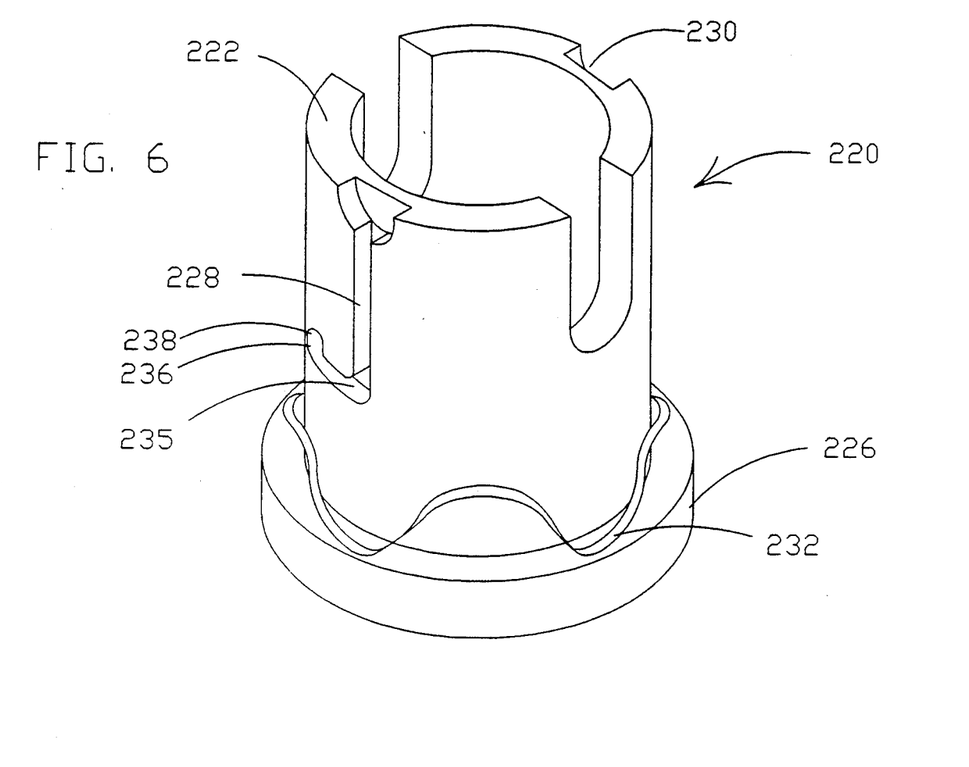
FIG. 6 illustrates in perspective view a shroud insert which in spring loaded for locking within a shroud of the design of FIG. 5.

Further, with reference to FIG. 4, the process needle assembly 30, injector end fitting 50, injector body 80 with second needle assembly 120 and docking ring 140 are illustrated in complete assembly one with each other and further in assembly with a shroud 160 which is secured to injector body 80. Further illustrated as carried within the interior of the shroud is an insert ring 174 which is secured within the interior of the shroud by self-tapping screws 180 which pass through orifices 178 and tap into insert 174. FIGS. 5 and 6 illustrate an alternate embodiment of a shroud body and insert ring by which an insert ring may be inserted and locked in place within the shroud body by spring loading.

Figure 2:
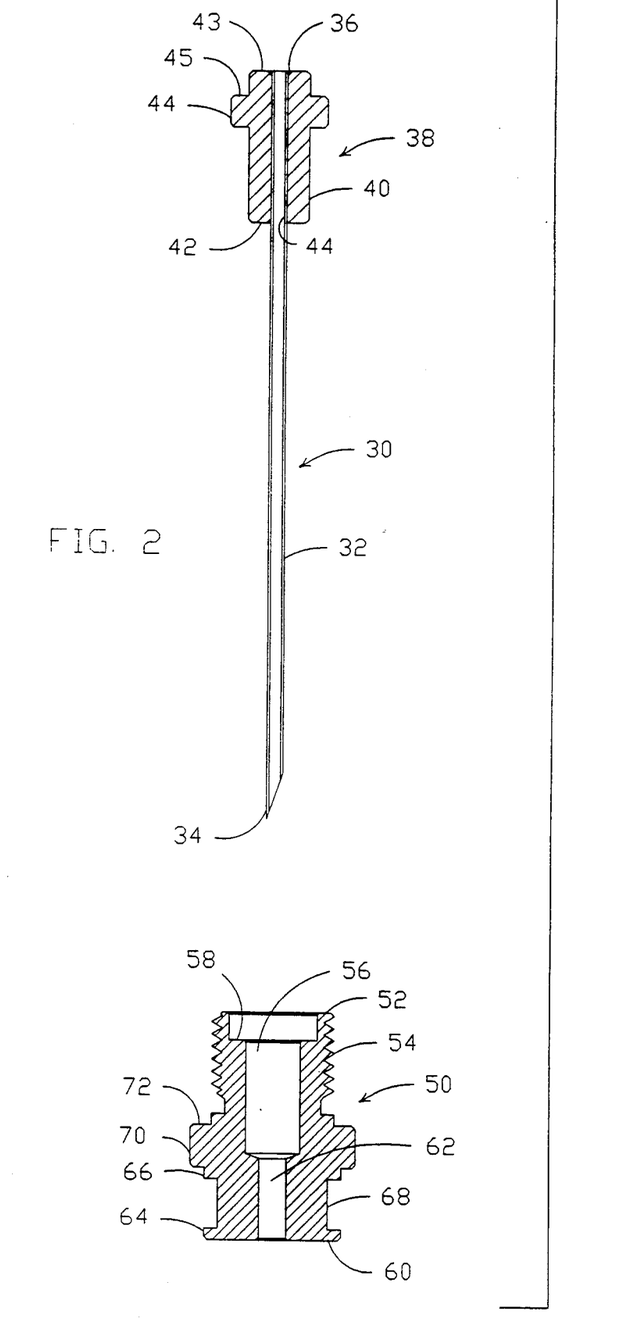
FIG. 2 illustrates in cross-sectional view the process needle assembly and an injector end fitting components of this invention.

With reference to FIGS. 1 and 2, the process needle assembly 30 comprises a hollow needle 32 having a sharp terminus end 34 and a mating end 36. A seating collar 38 comprising a sleeve body 40 having a central axial orifice 44 which communicates the lower end 42 and upper end 43 of the sleeve body is securely affixed about the mating end of hollow needle 32. Intermediate between its lower and upper ends a flange 44 is provided on the sleeve body. The upper shoulder 45 of this flange is positioned with respect to the upper end 43 of the sleeve body to provide a length therebetween which is substantially identical to the length of chamber 29 of the ball valve. Preferably the outside diameter of the upper end 43 of sleeve body 40 is substantially identical to the inside diameter of chamber 29 of the ball valve. The hollow needle may be constructed of any metallic material which is suitable to the corrosion resistance requirements of the fluid to be sampled. Accordingly, the hollow needle 32 may be constructed of a standard 316 stainless steel, Hastelloy B2 and C4, Inconel 625, titanium grade 2 or other metallic materials as may be necessary for corrosion resistance considering the fluid sample to be taken. Seating collar 38 may be fashioned of a like material.

Still with reference to FIGS. 1 and 2, the injector end fitting 50 is the component which receives the process needle assembly for purposes of securing it to the valve body in proper position to the ball of the valve. Injector end fitting 50 comprises a first end 52, the exterior surface of which 54 is threaded with a threading which is congruent to the internally threaded recess 28 of ball valve 10. The first end of the injector end fitting is provided with a collar seating cavity 56 which is configured to have a flange seating shoulder 58 and is dimensioned to correspond to the external dimensions of flange 44 and sleeve 40 of the seating collar 38 of the process needle assembly 30. The seating cavity 56 is communicated by a needle passage bore 62 to the second end 60 of the injector end fitting 50. The external surface of the second end of injector end fitting 50 is provided with a locking nut receiving recess 68 such that the recess defines the second end of the injector end fitting to have a radially outward projecting lower lip 64 and upper lip 66. The injector end fitting is further provided with a flange 70 which defines an upper stop shoulder 72. The injector end fitting is preferably dimensioned such that the distance between upper stop shoulder 72 of flange 70 and the first end 52 of the injector end fitting are of a length such that when assembled with ball valve 10, the first end of the injector end fitting will position the needle mating end 36 of the process needle assembly 30 to within from about 0.001 to about 0.01 inches of the external surface of the ball 18 of the ball valve. The closer the tolerance the less is the dead hole-up space between the valve ball and mating end of the sample needle, hence the less hold-up liquid volume from a previously taken liquid sample. The injector end fitting may be fabricated of a metallic material similar to that of the hollow needle.

Figure 3:
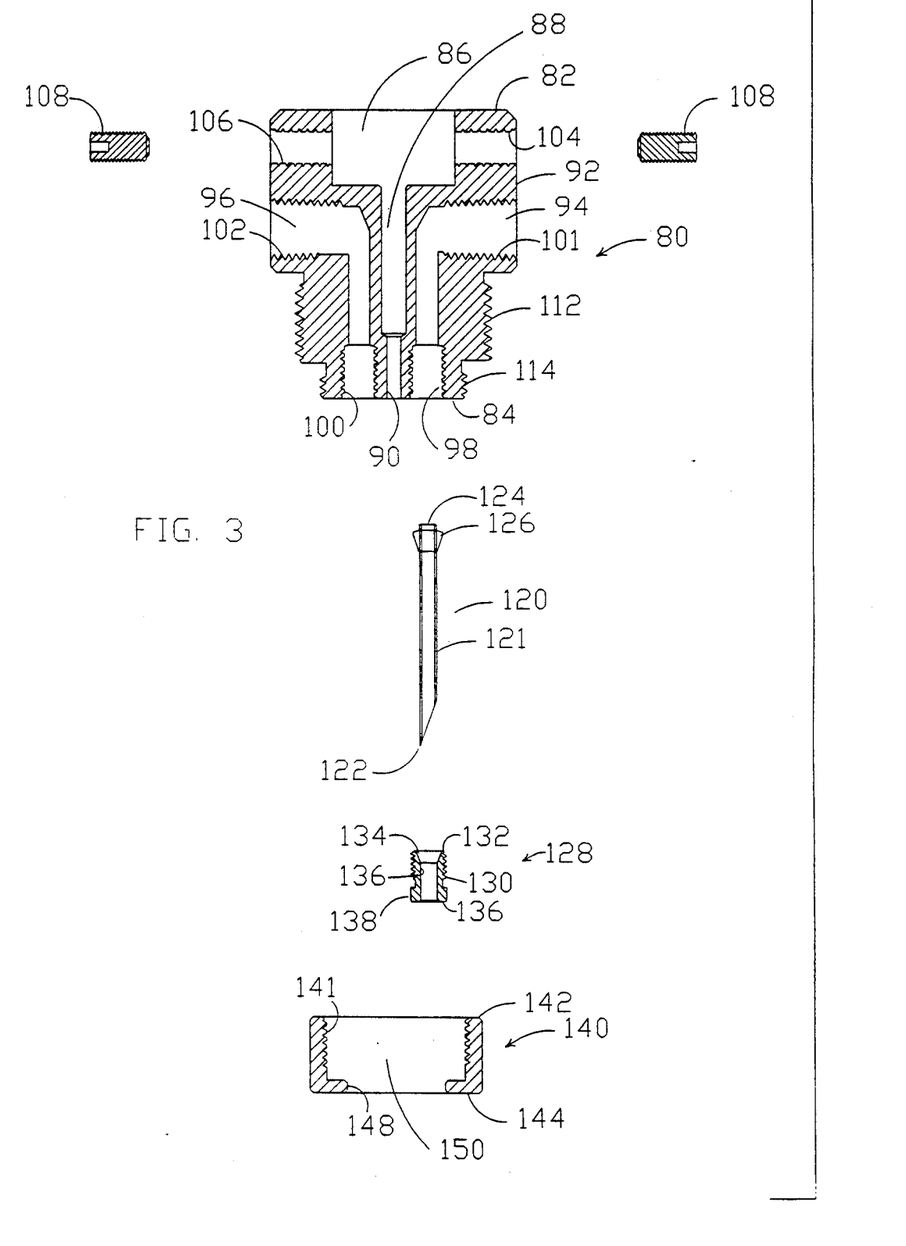
FIG. 3 illustrates in cross-sectional view the injector body, second or vent needle assembly, second needle locking nut and docking ring components of this invention.

With reference to FIG. 3, the injector body 80 has a first end 82 and a second end 84. The first end of the injector body is provided with a receiving cavity 86 which is dimensioned to conform with the diameter of the lower lip 64 and upper lip 66 of the injector end fitting (FIG. 2). An axially central bore 88 is provided in injector body 80 which communicates receiving cavity 86 with the second end 84 of the injector body. The dimensions of this bore are at least large enough to permit passage of the hollow needle 32 therethrough of the process needle assembly (FIG. 2). As illustrated, the bore is comprised of segments of two different diameters, the terminus of this bore 90 being of an inside diameter which is congruent with the outside diameter of the hollow needle. This is an expedient to simplify the machining of the bore. Injector body 80 is provided with a first and second passageway, 94 and 96, which communicate the second end 84 of the injector body to a side surface 92 of the injector body. At least one, and preferably both, of such passageways are provided at their terminus end which coincides with the second end of the injector body with a threaded female surface 98 and 100. Both passageways at their side terminus end are provided with threaded female fitting surfaces 101 and 102. The injector body 80 is further provided with one, and preferably more, internally threaded passageways 104 and 106 which extend from side surface 92 through and into the receiving cavity 86. By this means, locking screws 108 may be used to secure and affix the position of injector body 80 to injector end fitting 50 when those two components are in full assembly. With reference to FIGS. 2 and 3, the locking screws 108 affix the injector body 80 to the injector end fitting 50 both by frictional engagement with the locking nut receiving recess surface 68 and, should the threaded tension on one or more of the locking nuts be lost, by interference engagement with upper lip 66 of the needle collar body.

With reference to FIG. 3, the lower portion of injector body 80 is provided with a first externally threaded surface 112 which is intermediate between the first and second ends of that body, and with a second externally threaded surface 114 which is contiguous with the second end 84 of that body. The first externally threaded surface is larger in diameter than the second externally threaded surface.

Still in reference to FIG. 3, a second needle assembly 120 is provided which comprises a hollow needle 121 having a sharp terminus end 122 and a mating end 124. A ferrule 126 is securely affixed about the mating end 124 of needle 121. Further provided is a second needle locking nut 128 having a first end 132 and a second end 136. The first end of such locking nut has an externally threaded surface 130 which is congruent to the threading of the threaded female surface 98 of the injector body 80. The first end of the locking nut is provided with a ferrule receiving surface 134 which is communicated by orifice 136 to the second end of such locking nut. The external surface 138 of the second end of such locking nut is configured to be a tool engageable surface, such as a hexagonal exterior surface.

Further illustrated in FIG. 3 is docking ring 140 which has a first end 142 and a second end 144. The internal surface 141 of docking ring 140 is threaded from a point beginning with the first end 142 and extending towards second end 144. The second end of docking ring 140 is provided with a radially inwardly projecting lip 148 the periphery of which defines an orifice 150.

Since the injector body 80, locking screws 108, needle locking nut 128, and docking ring 140 are never exposed to process fluids or the vent vapors therefrom, these parts may be fabricated of non-exotic metallic materials such as 316 SS. Depending upon the type of process fluid to be sampled, only the second hollow needle 121 may need to be fabricated of an exotic metallic material for purposes of corrosion resistance similar to the material of which hollow needle 32 is fabricated.

FIG. 4 illustrates in assembly with a ball valve and with each other the process needle assembly 30, injector end fitting 50, injector body 80, second needle assembly 120 and needle locking nut, and docking ring 140. FIG. 4 further illustrates a shroud 160 which has an interiorly threaded surface 166 at its upper end 162. The threading of surface 166 is congruent to the threading of the first externally threaded surface 112 of injector body 80 (FIG. 3). The lower end 164 of shroud 160 is open. A plurality of orifices 178 are provided in the shroud body through which self-tapping screws 180 may be passed to secure a ring insert 174 within the shroud. Preferably, when assembled with an injector body 80 a jam or panel nut 190 is provided between the shroud and injector body which provides for easy positioning of viewing slots 176 (phantom lining) to a proper position for sample viewing. The shroud body is further provided with two pivot connectors 172 at a position 180° apart form each other which connect a sample container support strap 170 to the shroud body for pivotal movement. Preferably the shroud body is provided with a slot 176 to permit viewing of a sample container 185 when positioned within the shroud. The shroud is preferably fabricated of a metallic material, such as 316SS.

Although shroud 160 may be utilized without a ring insert 174, a ring insert is preferred. The ring insert 174 is preferably comprised of a polymeric material, such as PVC, PVDF, Teflon or the like and is dimensioned of an inside diameter similar to the outside diameter of a sample container for which the ring is designed to be used. Employment of a plastic ring insert is preferred because it prevents contact of a glass sample container with the metal shroud to reduce the chance of container breakage, it properly positions the septum 186 of the container for docking with and penetration by the process and vent needles, and it provides for a smooth movement of the container into contact with the needles. Once in place the sample container support strap 170 may be pivoted into place to support the container within the shroud.

FIGS. 5 and 6 illustrate an alternate embodiment for shroud 160 and a ring insert 220 whereby the insert may be locked in place by spring loading. In this embodiment the shoulder screws 172 of the shroud provide tabs 210 to guide the ring insert into the interior surface 168 of shroud 160 by registry with slots 228 and 230 of the insert shown in FIG. 6. The insert 220 is fabricated with a flange 226 at its lower end the outside diameter of which is preferably equal to the outside diameter of shroud 160. The external surface of insert 220 is provided with a plurality of grooves 228 and 230, preferably two diametrically opposed grooves, which extend axially from the upper end 222 of the inert towards the flanged end 226 to a point 235 intermediate therebetween. At this point 235 the groove is then extended circumferentially to point 236 along the external surface at which point the groove is extended axially towards the upper end 222 of the insert to point 238 at which point the groove terminates. The width and depth of the groove is at least equal to or greater than the width and length of the projection of the tabs of shoulder screws 172 which extend within shroud 160. A spring 232, preferably a wave spring, of a diameter greater than the outside diameter of the upper end 222 of insert 220 and less than the outside diameter of shroud 160 is positioned upon flange 226 of insert 220. The inside diameter of insert 220 may be of any desired dimension, depending upon the size of sample container for which a particular insert is designed.

Insert 220 is positioned within shroud 160 by inserting the insert through the open end 164 of the shroud until the upper end 222 of insert 220 contacts a tab of shoulder screws 172. The insert is then rotated until the shoulder screw tabs come into registry with grooves 228 and 230 and the insert is moved further into shroud 160 until tabs register with point 235 of the groove, the insert is then rotated until the tabs 210 register with point 236, thereafter inserting force on the insert is released. At the point wherein tabs 210 register with groove point 236 spring 232 is compressed between the insert flange 226 and shroud end 164. This spring tension exerts a downward force on flange 226 moving the insert downward and driving tabs 210 upward from groove point 236 to the groove end 238, thus locking the insert within the shroud by the interference engagement of tabs 210 with groove ends 238.

To remove an insert for purposes of replacement with another insert, such as one of a different inside diameter, the above described actions are performed in a reverse order.

Figure 7:
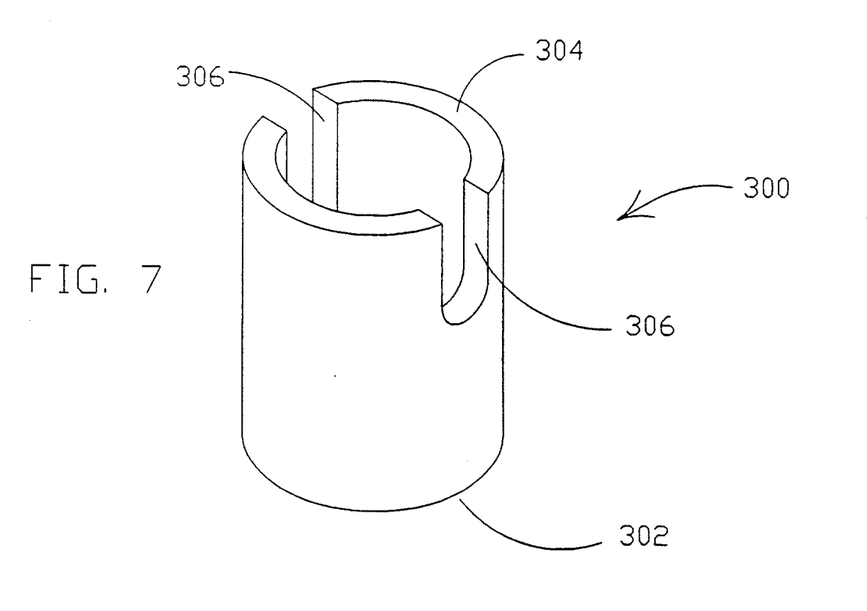
FIG. 7 illustrates sample container cup which may be used to accommodate sample containers of smaller size than the shroud.

With reference to FIG. 7, a further means is illustrated by which sample containers of a smaller diameter than that of shroud 160, or an insert 174 or 220 carried within the shroud, may readily be accommodated. This means comprises a cup 300 the lower end 302 of which is closed and the upper end 304 of which is open. Extending from upper end 304 to a point intermediate between the upper and lower end is one or more slots 306 which preferably are of a similar width as slot 170 of the shroud. The external diameter of the cup is of similar dimension to either the inside diameter of the shroud, or the shroud insert, as desired. The inside diameter of the cup is preferably tapered toward the closed end 302 so as to cause a tight friction fit between the bottle and the cup. The cup is used by placing a sample container in it then inserting the cup-container unit into the shroud such that the slots of the cup and shroud are in registry with each other, and continuing such insertion until the septum of the container is penetrated by the sample and vent needles of the sample collector device.

In the preferred embodiments of the sampler, it is preferred that the sharp terminus of the process needle extend beyond the sharp terminus of the vent needle. This insures that the sample container septum is penetrated by one needle at a time to minimize stress on the septum. It is further preferred that the vent needle be of a larger inside diameter than the sample needle. This reduces or eliminates the chance of inadvertently over-pressurizing the sample container.

To operate the sampler a process sample line is connected to the inlet and outlet ports 14 and 16 of the three-way ball valve. Normal operation allows flow of sample through the valve, so when an operator takes a sample, "fresh" product is flowing through the sample value.

When the operator takes a sample the operator simply secures a bottle in the shroud by pushing upward and forcing both needles through the septum into the bottle. The operator then turns the handle down on the three-way ball valve 180 degrees and process fluids flows down the process needle into the bottle The vapors in the bottle flow up the second or vent needle through the vent connection. These vapors can be neutralized at the sample point by going to an activated charcoal container or connected to some point the operator feels to be safe.

The operator upon completion of the sample acquisition simply returns the valve handle back to bypass position.

Although the invention has been described with reference to its preferred embodiments, those of skill in the art may from this description appreciate changes and modifications which can be made therein which do not depart from the scope and spirit of the invention as described and claimed hereafter.

We claim:

1. A mechanism for interconnecting a ball valve having a plurality of positions and an interior space of a sample container having a resealable septum closure, said mechanism comprising:

an injector end fitting having a first end having an exteriorly threaded valve fitting surface and an interior forming a needle collar seating cavity, a second end, and a bore which communicates said second end with the needle collar seating cavity, a hollow needle having a sharp terminus and a mating end, a needle seating collar comprising a sleeve body having a flanged end and an orifice which is securely affixed about the mating end of said needle;

an injector body having a first and second end, said injector body first end formed with an injector end fitting receiving cavity, said injector body having an orifice therein which communicates said injector end fitting receiving cavity to said injector body second end, said injector body having a first fluid passageway which communicates said injector body second end to a side surface of said injector body at a point intermediate between said injector body first and second ends, and a second fluid passageway which communicates said injector body second end to a side surface of said injector body at a point intermediate between said injector body first and second ends, at least one end of said first and second fluid passageway which terminates with the second end of said body being interiorly threaded.

2. The mechanism of claim 1, wherein said injector body further has a plurality of internally threaded passageways which communicate an exterior surface of said injector body with said needle collar receiving cavity.

3. The mechanism of claim 2, further comprising:

a second hollow needle having a sharp terminus and a mating end about which a ferrule is securely affixed;

a locking nut having a central orifice, one end of said nut having an exteriorly threaded surface and an interior ferrule receiving surface.

4. The mechanism of claim 3, wherein the second end of said injector body has a first and second exteriorly threaded surface, the first threaded surface being located intermediate between said first and second ends of said injector body, said second threaded surface contiguous to said injector body second end, and said first threaded surface being of greater diameter than the second surface.

5. The mechanism of claim 4, further comprising:

a docking collar comprising a ring having an interior surface which is threaded at a point beginning at a first end of the ring and extending towards a second end of the ring, the second end of said ring being formed with an inwardly projecting lip which defines an orifice in the second end of the ring.

6. The mechanism of claim 4, further comprising a shroud body, a first end of which contains an internally threaded surface adapted for threaded engagement to said first threaded surface of said injector body, and a second end which is open.

7. The mechanism of claim 6, wherein said shroud is adapted to receive inserts of variable inside diameters.

8. The mechanism of claim 6 wherein said shroud body has a plurality of tabs extending radially inwardly from an interior surface of the shroud body and the mechanism further comprises:

an insert body having interior and exterior surfaces and an upper end and a lower flanged end of a flange diameter at least equal to the outer diameter of said shroud body, the exterior surface of said insert being of a diameter substantially similar to the interior diameter of said shroud body, said insert body having a plurality of slots extending axially from the upper end to a point intermediate between the upper and lower flanged ends and then circumferentially to a second point at which each slot thereafter extends axially back toward the upper end and terminates, said body having a central orifice which communicates the upper and lower flanged end of the insert, and resilient encompassing the insert body and carried on the lower flanged end of the insert body.

* * * * *